United States Patent
Sarkis, Jr. et al.

(10) Patent No.: US 8,061,594 B2
(45) Date of Patent: *Nov. 22, 2011

(54) DEACTIVATABLE/REACTIVATABLE SMART CARD RECORDING APPARATUS

(75) Inventors: Frederick W. Sarkis, Jr., Rochester, NY (US); Joseph O. Sarkis, Vancouver (CA); Lisa Goodwin, Penfield, NY (US)

(73) Assignee: PharmaSmart LLC, Rochester, NY (US)

( * ) Notice: Subject to any disclaimer, the term of this patent is extended or adjusted under 35 U.S.C. 154(b) by 618 days.

This patent is subject to a terminal disclaimer.

(21) Appl. No.: 12/196,021

(22) Filed: Aug. 21, 2008

(65) Prior Publication Data

US 2009/0039153 A1 Feb. 12, 2009

Related U.S. Application Data

(63) Continuation-in-part of application No. 11/502,738, filed on Aug. 11, 2006, now Pat. No. 7,438,223.

(60) Provisional application No. 60/708,125, filed on Aug. 12, 2005.

(51) Int. Cl.
*G06K 5/00* (2006.01)
(52) U.S. Cl. .................................................... 235/380
(58) Field of Classification Search .............. 235/380, 235/385, 451, 492
See application file for complete search history.

(56) References Cited

U.S. PATENT DOCUMENTS

| 5,793,027 A * | 8/1998 | Baik .......................... 235/380 |
| 6,283,369 B1 | 9/2001 | Kurokawa et al. |
| 6,378,073 B1 | 4/2002 | Davis et al. |
| 6,524,240 B1 | 2/2003 | Thede |
| 6,563,596 B1 | 5/2003 | Narushima |

\* cited by examiner

*Primary Examiner* — Seung Lee
(74) *Attorney, Agent, or Firm* — Hiscock & Barclay, LLP

(57) ABSTRACT

An automated system with one or more memory-card interface devices, a custom-formatted end-user memory card keeps track of the user's results, and a reactivation memory card controls the provider's recharging of the end-user memory card after the end-user memory card expires. The contents of the reactivation memory card are updated in order to track its use by the provider of the readings.

20 Claims, 7 Drawing Sheets

FIG. 3A

|    | 0 | 1 | 2 | 3 | 4 | 5 | 6 | 7 | 8 | 9 | A | B | C | D | E | F |
|----|---|---|---|---|---|---|---|---|---|---|---|---|---|---|---|---|
| 00 | S1 | Ver | E0 | Phar | dd | mm | yy | | | | | Lang | | | | |
| 10 | | | | | | | | | | | | | | | | |
| 20 | | | | | | | | | | | | | | | | |
| 30 | | | | | | | | | | | | | | | | |
| 40 | | | | | | | | | | | | | | | | |
| 50 | | | | | | | | | | | | | | | | |
| 60 | | | | | | | | | | | | | | | | |
| 70 | | | | | | | | | | | | | | | | |
| 80 | | | | | | | | | | | | | | | | |
| 90 | | | | | | | | | | | | | | | | |
| A0 | | | | | | | | | | | | | | | | |
| B0 | | | | | | | | | | | | | | | | |
| C0 | | | | | | | | | | | | | | | | |
| D0 | | | | | | | | | | | | | | | | |
| E0 | | | | | | | | | | | | | | | | |
| F0 | | | | | | | | | | | S2 | S3 | S4 | S5 | S6 | |

| | | |
|---|---|---|
| Sn | Security Code n (1-6) | Start at 1, incremented as format changes |
| Ver | Smart Card Version Number | |
| User | User Type E0 | 00 - User; E0 - Recharge; FD - Technician; FE - OEM; FF - Developer |
| Phar | Pharmacy Code | Issuing pharmacy's code |
| # | Expiration Date | 1 year from initial use, dd/mm/yy date format |
| | Number of Readings on Card | 0 - 30 |
| Next | Next Reading Inserted Here | |
| | Number of Recharges Remaining | |
| Lang | Language | 0x00 - English, 0x01 - French, 0x02 - Spanish |
| | 30 Latest Readings | Last 10 printed, all 30 used for graph. dd/mm/yy - date of reading. D - diastolic pressure, S - systolic pressure, P - pulse rate |
| | Unused Control Data | Future expansion |
| | Unused Data | Future expansion |

FIG. 3B

DEACTIVATABLE/REACTIVATABLE SMART CARD RECORDING APPARATUS

CROSS-REFERENCE TO RELATED APPLICATIONS

This application is a continuation-in-part of U.S. patent application Ser. No. 11/502,738 filed Aug. 11, 2006 which claims priority to U.S. provisional application Ser. No. 60/708,125 filed Aug. 12, 2005.

BACKGROUND

The invention relates to authorizing, recording and tracking usage, and more specifically to the use of two variable "smart cards" to store result information.

SUMMARY

Automated blood pressure (ABP) machines and other types of non-invasive medical self-monitoring equipment, e.g., automated glucose monitors, cholesterol monitors, blood oxygen monitors are either purchased or leased by pharmacies, corporate work sites, health clubs and other customers. For the purpose of this discussion, these customers will be referred to as "Locations".

The Locations provide ABP and other medical self-monitoring machines as a service to their customers, employees, members, etc. For the purpose of this discussion, we will refer to these customers, employees, and members using the ABP or other medical self-monitoring machines as the "End User". Such Locations often offer the End User the option to use a memory card or a Smart Card to record and track their blood pressure history over time.

As used in this patent, the term "memory card" includes any device that is generally the size of credit card (2"×3.25") with power, ground, input and output ports or terminals and an array of memory cells arranged in rows and columns. Such memory cells are typically made of flash memory which are static memory devices that retain their information when electrical energy to the card is removed. Smart Cards include memory arrays of flash memory cells and have a microprocessor or other control or logic circuitry. One purpose of the microprocessor or other circuitry is to provide security for the data on the card. Such Smart Cards have encryption and decryption keys or stored programs that secure the card from unwanted access.

Each time the End User uses the memory card or Smart Card in the machine, the blood pressure reading, pulse rate, and the date of the measurement are recorded on the card. The ABP machine then prints out a history of the End User's most recent results (as many as 10 results), and provides a calculated average blood pressure and pulse rate for the End User.

Similar monitoring, data collection, data compilation, and data presentation opportunities exist for other forms of medical self-monitoring equipment. A printed history of the End User's most recent results for any such monitoring process is important as it provides the End User with information to share with physicians, pharmacists, and other health care professionals. Recorded ABP information assists the health care professional in evaluating the End User's blood pressure history and the effectiveness of any End User hypertension control program. Recorded glucose levels, cholesterol levels, blood oxygen levels, and other records of medical monitoring for the End User can likewise assist health care professionals in their care of that End User.

The invention enables the providers of automated blood pressure readings and other non-invasive physiological test data, such as pharmacies, corporate work sites, health clubs and other customers, to charge an annual fee for the use of a memory card or Smart Card to record the non-invasive physiological test data and make the data available for health consultations. The invention's software, installed in an automated blood pressure system or other medical self-monitoring system with one or more memory card or Smart Card interface devices, uses a custom-formatted end-user memory card for keeping track of the user's non-invasive physiological test data and the dates these readings were taken. The software also uses a reactivation memory card for controlling the provider's recharging of the end-user memory card. The invention's processing reactivates the end-user memory card or Smart Card after it expires, and updates the contents of the reactivation memory card in order to track the number of reactivations provided.

The invention's apparatus and methods also apply to non-medical systems for recording readings and verifying usability.

BRIEF DESCRIPTION OF THE DRAWINGS

FIG. 3A shows the format of the data stored on the User Smart Card prior to encryption. A memory map of the encrypted card is not shown as the encryption techniques are well known in the art.

FIG. 3B shows the format of the data stored on the Reactivation Card.

DETAILED DESCRIPTION

In one embodiment, the invention is both an apparatus and a process, developed initially for the PharmaSmart Model PS-2000 blood pressure machine and similar machines made by others. The PS-2000 is equipped to use blood pressure Smart Cards to store blood pressure readings for the End User. The parameters of usage for this embodiment is the reading and blood pressure information. It is likely that millions of these blood pressure Smart Cards will eventually be in circulation in North America and in other parts of the world. The invention provides the option for Locations to: 1) generate additional revenues by charging the End User an annual fee for use of the Smart Card, and 2) provide End User with at least one annual blood pressure consultation.

The use of the invention is as follows. The Location issues a Smart Card to the End User. The first time the End User uses the Smart Card in the ABP machine, it electronically "stamps" a reactivation date onto the Smart Card. The reactivation date is a fixed or variable date, but preferably is one (1) year from the date of first use in the machine. This means the End User has a full year of use of the Smart Card before it will require a reactivation. If the card is not reactivated by the reactivation date, it will no longer work in the ABP machine.

At any time, the Location may purchase reactivation credits directly from manufacturer of the ABP machine. These credits are loaded onto a unique "Reactivation Smart Card", and shipped directly to the Location. Upon the End User's request, the Location personnel can use the Reactivation Smart Card to reactivate the End User's card for an additional year. In order to do this the Location personnel must have both the Reactivation Smart Card and the End User Smart Card in hand. They then simply insert the Reactivation Smart Card into the ABP machine and follow the instructions provided on the machine's display. Once completed, an updated reactivation date is electronically "stamped" onto the End User Smart Card providing another full year of use of the Smart Card. Each time the Location personnel reactivates an End User Smart Card, the Reactivation Smart Card is debited one (1) reactivation credit. Once all of the reactivation credits are used, the Location personnel discards the Reactivation Smart Card and, as required, may order an additional Reactivation Smart Card from the ABP machine manufacturer. In an alternative embodiment, the machine is capable of loading additional credits onto the Smart Card.

The ABP machine manufacturer may charge Locations a fee for each reactivation credit they order, and the Location, in turn, can charge the End User an annual fee for the User Smart Card.

Figure 1A:
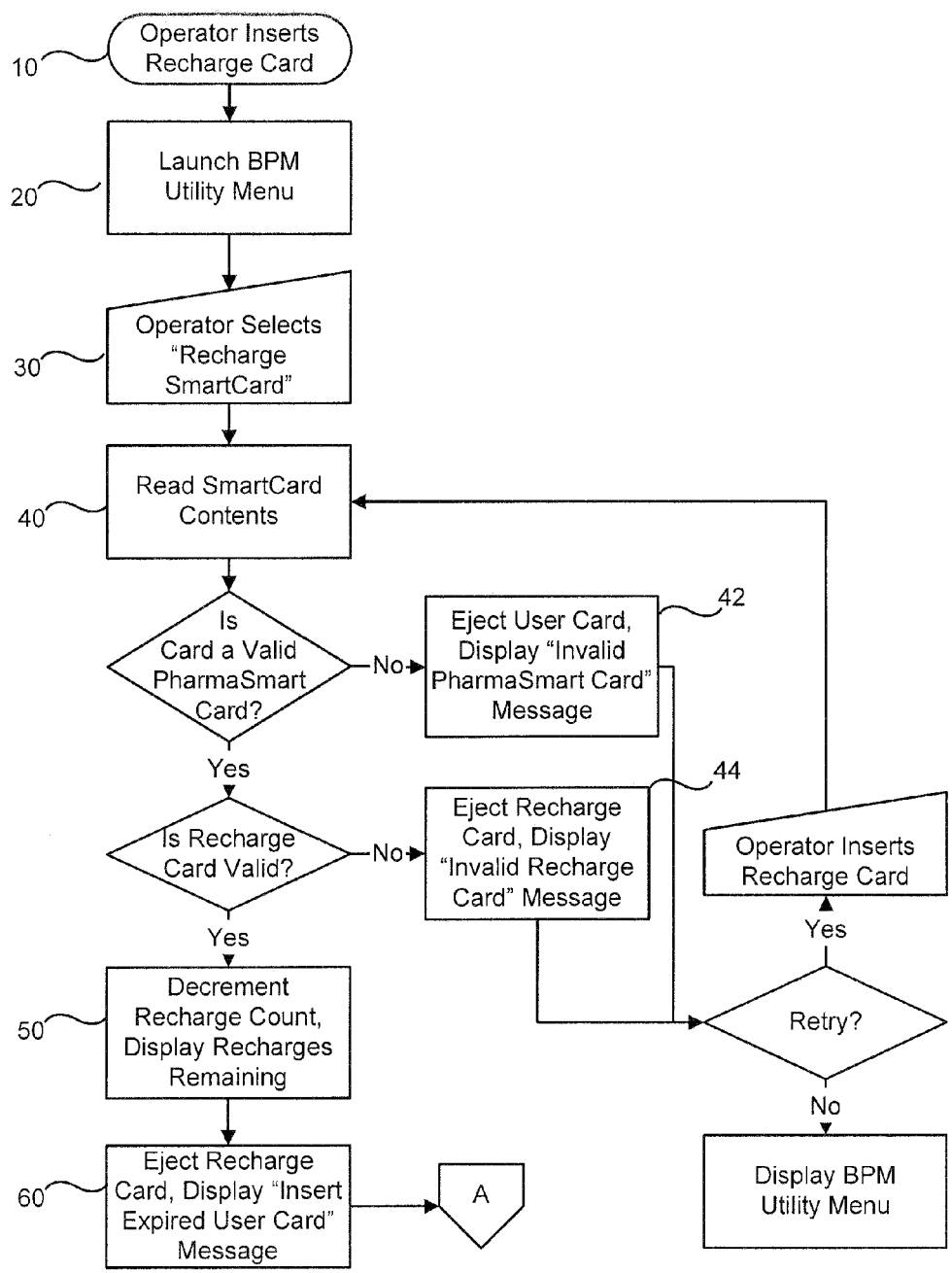
FIG. 1A shows the processing flow of steps for updating a Reactivation Card using a single-port card reader.
Figure 1B:
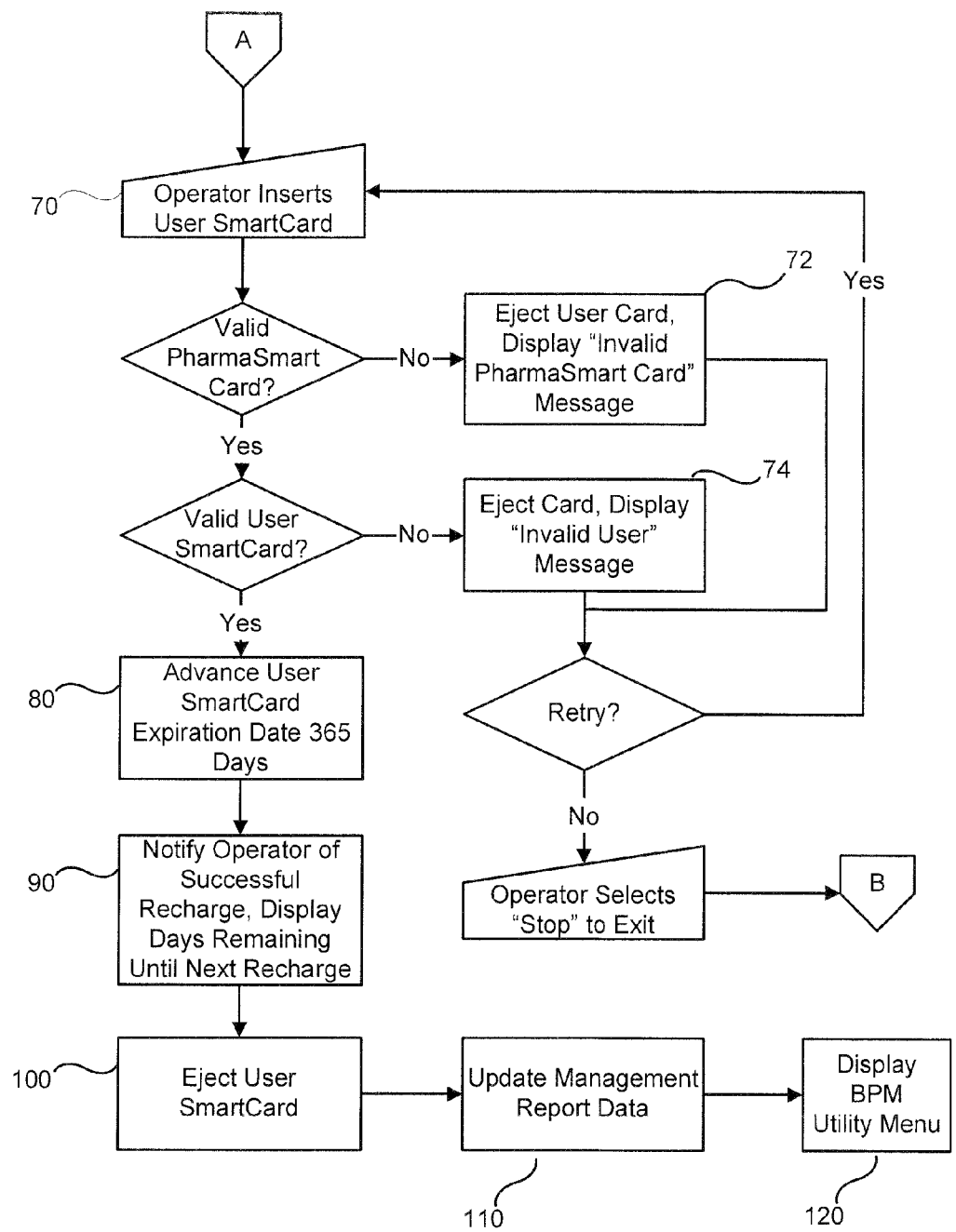
FIG. 1B shows the processing flow of steps for recharging a User Smart Card using a single-port card reader.
Figure 1C:
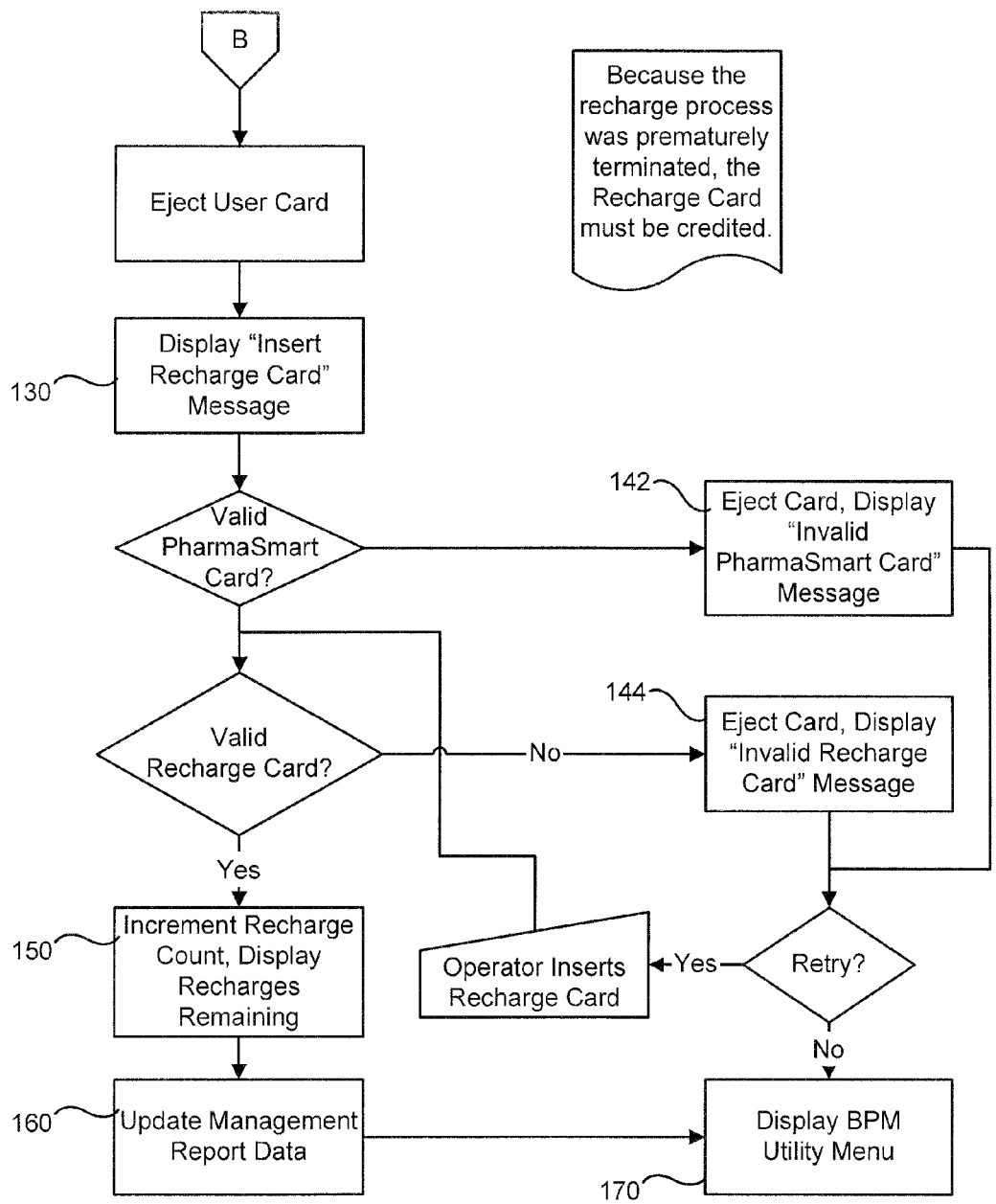
FIG. 1C shows the processing flow of steps for correcting the Reactivation Count on a Reactivation Card using a single-port card reader.
Figure 3A:
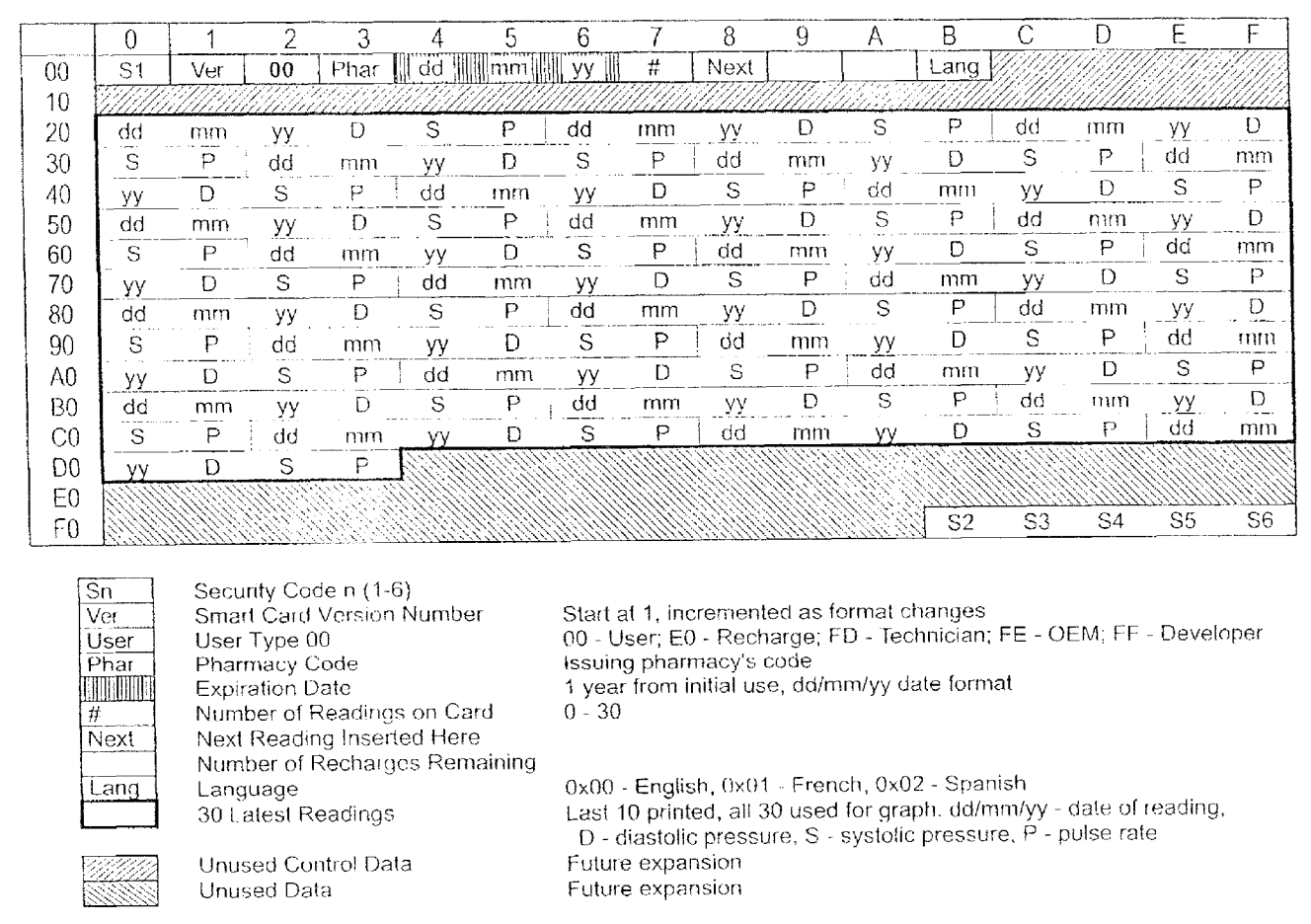

FIGS. 1A through 1C show a combined flow chart presenting specific software design and operational details of the Smart Card reactivation process as performed using a single-port card reader. There are three overall parts of the reactivation process: 1) updating the Reactivation Card, 2) updating the User Smart Card, and 3) restoring the Reactivation Card to an earlier state when a User Smart Card update has not been completed. FIG. 1A shows the basic steps of the updating of a Reactivation Card. Refer to FIG. 3A for the data memory map for the data fields stored on the User Smart Card (User Type '00') and to FIG. 3B for the data fields stored on the Reactivation Card (User Type 'E0').

1. The operator inserts (10) the Reactivation Card in the card reader.
2. The system presents (20) the BPM utility menu to the operator.
3. The operator selects (30) the "Reactivation Smart Card" option from the menu.
4. The system reads (40) the Reactivation Card contents. If the card is not a valid PharmaSmart card of any type, the system displays (42) a message to that effect and prompts the user to use a PharmaSmart Reactivation card.
5. If the card is a valid PharmaSmart card but not a Reactivation Card, the system displays (44) a message to that effect and prompts the user to use a PharmaSmart Reactivation card.
6. If the card is a valid PharmaSmart Reactivation Card, the system decrements (50) the card's Reactivation Count, and displays the number of reactivations remaining on the card.
7. The system ejects the Reactivation Card and prompts (60) the operator to insert the User Smart Card.

Once the Reactivation Smart Card is decremented one credit, the User Smart Card updating process begins. See FIG. 1B for the steps:

1. The operator inserts (70) the User Smart Card.
2. If the card is not a valid PharmaSmart card of any type, the system displays (72) a message to that effect and prompts the user to use a PharmaSmart user Smart Card.
3. If the card is a valid PharmaSmart card but not a User Smart Card, the system displays (74) a message to that effect and prompts the user to use a PharmaSmart User Smart Card.
4. If the card is a valid PharmaSmart User Smart Card, the system advances (80) the card's Expiration Date by 365 days, or if the Expiration Date has passed, sets a new Expiration Date 365 days from the User Smart Card's update.
5. The system notifies (90) the operator of the successful update and displays the total number of days until the User Smart Card will require another reactivation.
6. The system ejects (100) the User Smart Card.
7. The system updates (110) its management report data.
8. The system displays (120) the BPM Utility Menu.

During the User Smart Card update, the operator may decide that the reactivation process cannot be completed. If the process is not completed, the Reactivation Card and the User Smart Card are left in states that are mutually inconsistent. The Reactivation Card indicates that a reactivation has been done, while the User Smart Card has not been reactivated. Consequently, the inconsistency should be corrected. The Reactivation Card should be incremented one Reactivation Credit.

See FIG. 1C. The steps:

1. The system prompts (130) the operator to insert the Reactivation Card.
2. The system reads the Reactivation Card contents. If the card is not a valid PharmaSmart card of any type, the system displays (142) a message to that effect and prompts the operator to use a PharmaSmart Reactivation card.
3. If the card is a valid PharmaSmart card but not a Reactivation Card, the system displays (144) a message to that effect and prompts the operator to use a PharmaSmart Reactivation card.
4. If the card is a valid PharmaSmart Reactivation Card, the system increments (150) the card's Reactivation Credits by one credit, and displays the number of Reactivation Credits remaining on the card.
5. The system updates (160) its management report data.
6. The system displays (170) the BPM Utility Menu.

Figure 2A:
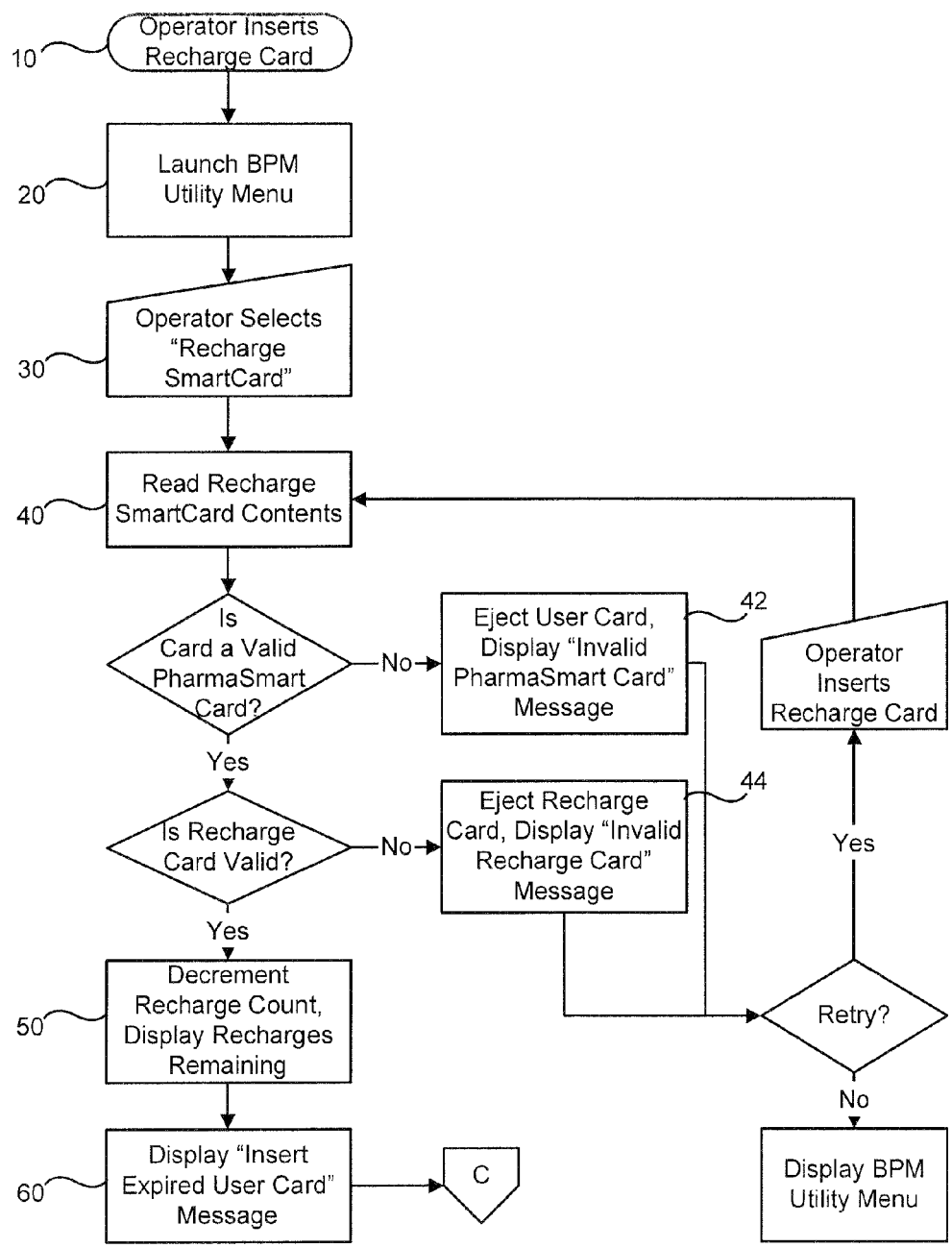
FIG. 2A shows the processing flow of steps for updating a Reactivation Card using a dual-port card reader.
Figure 2B:
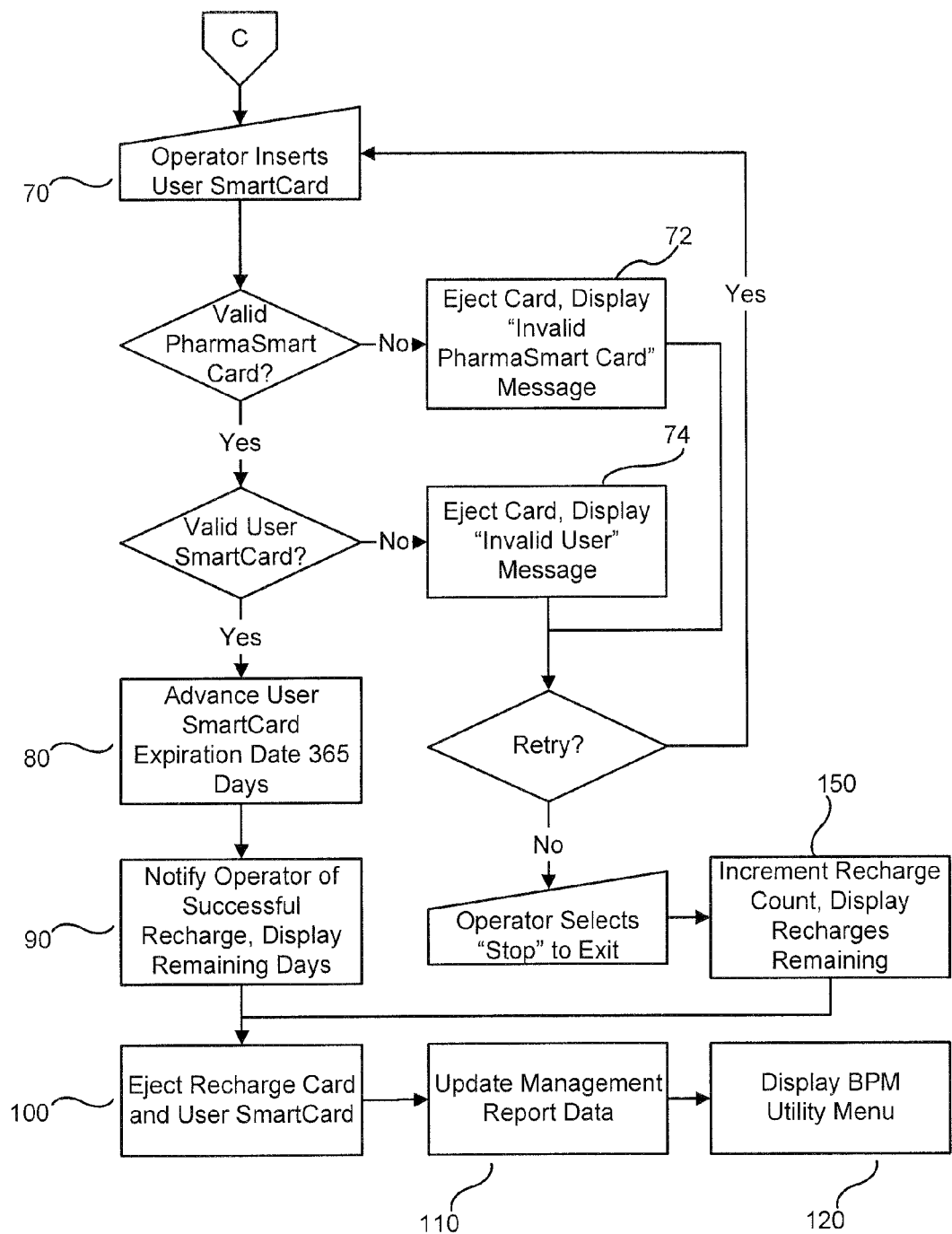
FIG. 2B shows the processing flow of steps for recharging a User Smart Card and correcting the Reactivation Count on a Reactivation Card using a dual-port card reader.

In an alternative embodiment of the system, a dual-port card reader allows the Reactivation Card to remain accessible to the system while the User Smart Card is being updated. In this alternative dual-port embodiment, Step 4 of FIG. 1C is done as part of the process of FIG. 1A after the operator has interrupted the User Smart Card update, and the entire process is simplified as shown in FIGS. 2A and 2B. This alternative dual-port embodiment, while more expensive in hardware terms, has the advantage of eliminating all manual steps for correcting the inconsistency between the Reactivation Card and the User Smart Card.

FIG. 2A shows the basic steps of the updating of a Reactivation Card:

1. The operator inserts (10) the Reactivation Card in the Reactivation card reader slot.
2. The system presents (20) the BPM utility menu to the operator.
3. The operator selects (30) the "Reactivation Smart Card" option from the menu.
4. The system reads (40) the Reactivation Card contents. If the card is not a valid PharmaSmart card of any type, the system displays (42) a message to that effect and prompts the user to use a PharmaSmart Reactivation card.

8. If the card is a valid PharmaSmart card but not a Reactivation Card, the system displays (44) a message to that effect and prompts the user to use a PharmaSmart Reactivation card.
9. If the card is a valid PharmaSmart Reactivation Card, the system decrements (50) the card's Reactivation Count, and displays the number of reactivations remaining on the card.
10. The system prompts (60) the operator to insert the expired User Smart Card in the User Smart Card card reader slot.

Once the Reactivation Smart Card is updated, the User Smart Card updating process begins. See FIG. 2B for the steps:

1. The operator inserts (70) the User Smart Card in the User Smart Card reader slot.
2. If the card is not a valid PharmaSmart card of any type, the system displays (72) a message to that effect and prompts the user to use a PharmaSmart user card.
3. If the card is a valid PharmaSmart card but not a User Smart Card, the system displays (74) a message to that effect and prompts the user to use a PharmaSmart User Smartcard.
4. If the card is a valid PharmaSmart User Smart Card, the system advances (80) the card's Expiration Date by 365 days, or if the Expiration Date has passed, sets a new Expiration date 365 days from the User Smart Card's update.
5. If the operator has interrupted the User Smart Card update process without change to the User Smart Card's Expiration Date, the system increments (150) the Reactivation Card's Reactivation Count, displays the number of reactivations remaining on the card.
6. If the operator has completed the User Smart Card update process successfully, the system notifies (90) the operator of the successful update and displays the new expiration date placed on the card.
7. The system ejects (100) the User Smart Card.
8. The system ejects (100) the Reactivation Card
9. The system updates (110) its management report data.
10. The system displays (120) the BPM Utility Menu.

Regarding Step 2. identifying a valid PharmaSmart card, the format defined in FIG. 3 contains values in 'Security Code', 'Smart Card Version Number', 'User Type', 'Pharmacy Code', and 'Expiration Date' that may be used in combination in ways well-known in the art to identify the card as a valid PharmaSmart card.

Regarding Step 3. distinguishing between the Reactivation Card and the User Smart Card, the formats of the Reactivation Card and the User Smart Card are the same, as shown in FIG. 3, except that the Reactivation Card contains an 'E0' code in the User Type field, while the User Smart Card contains a '00' in the User Type field. Also, since the Reactivation Card is not used for storing readings, the 'Number of Readings on Card', 'Next Reading Inserted Here', and the '30 Latest Readings' on the Reactivation Card will not contain valid data unless such data is added by another application.

See FIGS. 3A and 3B. The User Type field may contain codes that identify other special-purpose card formats as needed for conventional technical and developmental purposes. FIG. 3A shows a map of the memory card. Such cards may be used in the invention but they do not provide security for the data on the card. But they are less expensive than the more secure Smart Cards and can store the same user data that is stored on a Smart Card.

In a general embodiment providing for storage and analysis of non-invasive physiological test data and other medical monitoring information, the invention's User Smart Card records values from automated equipment for reading blood glucose level, blood cholesterol level, or other testable medical parameter values. The range of testable medical parameter values expands constantly as new technologies enable rapid, reliable, low-powered monitoring techniques to be packaged and made available to an End User.

The User Smart Card records the non-invasive physiological test data that the user took over the course of a year. The user can use the User Smart Card to access this entire history at any Location, and print out the most recent 10 entries or all of them. The average of the printed entries is given with the printout. The date of each reading is also recorded on the User Smart Card and printed alongside each entry, allowing the user or a physician to identify trends in the data. Additionally, at the user's request, the data from the User Smart Card can be loaded into the computer system of a pharmacy or doctor's office, allowing health care workers quick access to the user's non-invasive physiological test data.

At a Location, the user can print out the entire history of non-invasive physiological test data stored on the user Smart Card. Additionally, at a pharmacy or physician's office this data can be submitted for a consultation on the patient's condition. When the User Smart Card is reactivated, an option is given to allow the user to submit his data to a pharmacy for a consultation.

Tests now performed in a laboratory, such as blood enzyme levels for such critical markers as creatine phosphokinase (CPK), will eventually be capable of being performed properly and inexpensively in a manner similar to that now used for blood pressure monitoring. Furthermore, evaluations requiring significant analysis and processing of data, such as the classification of cardiac arrhythmias requiring medical attention, may become capable of being performed in a consumer setting as well.

Finally, numerous drugs, such as the COX-2 inhibitors, can produce varied deleterious effects on small subsets of their users. The monitoring of blood markers for adverse or allergic reactions to such drugs presents another field of application for the present invention.

To record the values captured, the invention substitutes different value sets and ranges for different types of reading and different sensitivity requirements. For example, readings of blood glucose levels when fasting range from the 60-100 range (excellent) to above 180 (poor), but after a meal the range rises so that the 110-140 range represents an excellent level, while above 220 represents a poor level of blood glucose (source of values: University of Massachusetts Medical School Web page concerning self-monitoring of blood glucose levels using the lancet). Ranges for different classes of monitored values are represented in the invention using range classifications, biasing of values, elimination of non-significant digits of precision, and other techniques well-known in the art for compressing data values for storage in limited memory space.

In a secure embodiment, the invention incorporates conventional anti-tampering hardware and software components in the User Smart Card and the Reactivation Card to prevent an End User, a Location employee, or a thief from using a conventional standalone card reader to alter the contents of the User Smart Card or the Reactivation Card.

In the secure embodiment, the invention applies encryption to the contents of the card, rendering the contents of the card unreadable by any process except the decryption of the encrypted values. The Location employee (for the Reactivation Card) or the End User (for the User Smart Card) reads and updates the card's contents by furnishing the decryption key for the card. The specific encryption techniques used are well-known in the art and so are not described here.

Any attempt to read the card's contents using a conventional standalone card reader triggers the execution of software which breaks open one or more fuses on the card, rendering the card useless. While such measures do not prevent fraudulent misuse of the card, they make such misuse considerably more difficult.

The operation, contents, encryption, and decryptions of the invention's Reactivation Card are the same for all classes of data to be collected.

In additional embodiments in the non-medical contexts, the apparatus gathers, stores, and recalls a limited number of data values on a reactivation basis as described hereinabove.

In one embodiment the apparatus is utilized in transit systems, wherein a machine charges a User Smart Card with travel credit increments deductible by the user at entry into each stage of a journey on a transit system using the invention. At each stage of the journey, the invention notes the time and location of the user's entry for travel, and deducts one or more credit increments as appropriate for the stage on which the user is embarking. The user may afterwards obtain from the Smart Card a record of travel for business or evidentiary reasons. Furthermore, the Smart Card can be set to expire on a particular date, for example, one year from the date of purchase.

In another embodiment the apparatus is utilized in libraries and lending systems, wherein a machine charges a User Smart Card with lending credit increments deductible by the user when borrowing a book, film, music score, or other item of rental or lease goods or equipment. Different items borrowed may result in different numbers of credit increments being deducted. The apparatus stores the time and date of lending or rental and the time and date of return of the item on the User Smart Card.

In yet another embodiment the apparatus is utilized in gaming facilities such as arcades, bowling allies or pool halls, wherein a machine charges a User Smart Card with credit increments deductible by the user accessing a game in the facility. Different games may result in different numbers of credit increments being deducted. The apparatus stores the time, date and duration of play.

While the apparatus has been described with reference to preferred embodiments, it will be understood by those skilled in the art that various changes may be made and equivalents may be substituted for elements thereof to adapt to particular situations without departing from the scope. For example the apparatus may be utilized for calling cards, cell phone rentals, copy machines, photo kiosks, music/video downloads, movie theaters, car rentals or any other area in which it is desirable to authorize and record usage data.

Therefore, it is intended that the apparatus not be limited to the particular embodiments disclosed as the best mode contemplated, but that the apparatus will include all embodiments falling within the scope and spirit of the appended claims.

What is claimed is:

1. An apparatus for authorizing, recording or tracking usage comprising:
   a machine for automatically detecting parameters of usage of a service, resource or object;
   means for recording parameters of the detected usage on a first transportable device adapted to receive and hold usage data;
   means for limiting the duration, number of uses, or both on the first transportable device to a first period of time, wherein the first transportable device ceases to allow usage once a predetermined limit for the first period of time is exceeded;
   means for reactivating the first transportable device to extend the first period of time to a second period of time;
   means for limiting the duration, number of uses made on the first transportable device, or combination thereof to a second period of time;
   wherein reactivating the first transportable device to extend the first period of time to a second period of time permits continued usage until a predetermined limit for the second period of time is reached.

2. The apparatus of claim 1 further comprising a means for preventing access to or alteration of the parameters of usage.

3. The apparatus of claim 1 wherein the means for recording parameters of the detected usage further comprising a reading and writing device.

4. The apparatus of claim 3 wherein the reading and writing device is selected from the group consisting of a flash memory reading and writing device, an optical memory reading and writing device and a magneto-optical memory reading and writing device.

5. The apparatus of claim 3 wherein the reading and writing device is an electronic smart card reading and writing device.

6. The apparatus of claim 1 wherein the means for limiting the duration further comprises an expiration date and time stored on the first transportable device.

7. The apparatus of claim 6 wherein the machine for automatically detecting parameters of usage further comprises a source of current date and time information.

8. The apparatus of claim 7 wherein the machine for automatically detecting parameters of usage further comprises a software program for comparing the current date and time information with the expiration date and time.

9. The apparatus of claim 1 wherein the usage data comprises the time, date, and location of the usage.

10. The apparatus of claim 1 wherein the usage data comprises the number uses available on the first transportable device.

11. The apparatus of claim 1 wherein the usage data comprises results of the usage.

12. The apparatus of claim 1 wherein the service, resource, or object is selected from the list consisting of:
    passage on a transit conveyance;
    borrowing of media;
    renting of an object;
    downloading of media;
    permitting access to an area;
    starting of a machine; and
    printing of media.

13. The apparatus of claim 1 wherein the means for preventing access to or alteration of the parameters of usage, further comprises a means for encryption of the recording parameters of the detected usage.

14. The apparatus of claim 13 wherein the means for preventing access to or alteration of the parameters of usage, further comprises a means for decryption of the recording parameters of the detected usage.

15. The apparatus of claim 1 wherein the means for preventing access to or alteration of the parameters of usage, further comprises a means for destroying the recording parameters of the detected usage.

16. An apparatus for authorizing usage comprising:
    a transportable device adapted to hold usage data, the usage data comprising a first expiration date and a number of uses available on the transportable device;

a machine for detecting the usage data on the transportable device;

means for recording usage data to the transportable device;

means for deactivating the transportable device after either the first expiration date or the number of uses available has been exceeded;

means for reactivating the transportable device to store a second expiration date or additional number of uses available on the transportable device;

a software program for decrementing the number of uses available on the transportable device upon each authorized usage.

17. The apparatus of claim 16 wherein the machine for automatically detecting parameters of usage further comprises a source of current date information and a software program for comparing the current date information with the expiration date.

18. The apparatus of claim 16 further comprising a means for preventing access to or alteration of the usage data.

19. The apparatus of claim 16 wherein the means for recording usage data to the transportable device further comprising a reading and writing device.

20. The apparatus of claim 16 wherein the usage data further comprises information about authorized usage.

* * * * *